(12) United States Patent
Butts et al.

(10) Patent No.: US 8,728,529 B2
(45) Date of Patent: May 20, 2014

(54) NANOPARTICLE CONTRAST AGENTS FOR DIAGNOSTIC IMAGING

(75) Inventors: Matthew David Butts, Rexford, NY (US); Robert Edgar Colborn, Niskayuna, NY (US); Peter John Bonitatibus, Jr., Saratoga Springs, NY (US); Amit Mohan Kulkarni, Clifton Park, NY (US); Bruce Allan Hay, Niskayuna, NY (US); Andrew Soliz Torres, Troy, NY (US); Brian Christopher Bales, Niskayuna, NY (US); Michael Ernest Marino, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 835 days.

(21) Appl. No.: 12/344,606

(22) Filed: Dec. 29, 2008

(65) Prior Publication Data

US 2010/0166665 A1 Jul. 1, 2010

(51) Int. Cl.
*A61K 9/14* (2006.01)
*A61K 9/51* (2006.01)
*A61K 49/04* (2006.01)
*A61K 49/06* (2006.01)

(52) U.S. Cl.
USPC ............ 424/489; 424/9.3; 424/9.32; 424/9.4; 424/9.42; 977/773; 977/905; 977/928; 977/930

(58) Field of Classification Search
None
See application file for complete search history.

(56) References Cited

U.S. PATENT DOCUMENTS

| 6,410,765 | B1 * | 6/2002 | Wellinghoff et al. ........... 556/10 |
| 7,138,468 | B2 | 11/2006 | McCormick, III et al. |
| 2004/0105980 | A1 | 6/2004 | Sudarshan et al. |
| 2007/0082190 | A1 | 4/2007 | Endres et al. |
| 2007/0122620 | A1 | 5/2007 | Bonitatebus, Jr. et al. |
| 2008/0089836 | A1 | 4/2008 | Hainfeld |
| 2008/0095699 | A1 | 4/2008 | Zheng et al. |

FOREIGN PATENT DOCUMENTS

WO 2007146680 A1 12/2007
WO WO 2007146680 A1 * 12/2007

OTHER PUBLICATIONS

M Ma, Y Zhang, W Yu, HY Shen, HQ Zhang, N Gu. "Preparation and characterization of magnetite nanoparticles coated by amino silane." Colloids and Surfaces A: Physicochem. Eng. Aspects, vol. 212, 2003, pp. 219-226.*
PCT International Search Report dated Dec. 14, 2010 and Written Opinion.
Fu et al., "Self-Assembled (SA) Bilyaer Molecular Coating on Magnetic Nanoparticles", Applied Surface Science, vol. 181, pp. 173-178, 2001.
Hak Soo Choi, Wenhao Liu, Preeti Misra, Eiichi Tanaka, John P Zimmer, Binil Itty Ipe, Moungi G Bawendi and John V Frangioni; "Renal clearance of quantum dots"; Nature Biotechnology vol. 25 No. 10 Oct. 2007; accepted Aug. 16; published online Sep. 23, 2007; Pages from 1165-1170; doi:10.1038/nbt1340.
Qiao Jin, Jian-Ping Xu, Jian Ji and Jia-Cong Shen; "Zwitterionic phosphorylcholine as a better ligand for stabilizing large biocompatible gold nanoparticles"; The Royal Society of Chemistry 2008; First published as an Advance Article on the web Apr. 22, 2008; DOI: 10.1039/b801959b; Chem. Commun., 2008, 3058-3060.
Ya Ding, Xing-Hua Xia and He-Sheng Zhai; "Reversible Assembly and Disassembly of Gold Nanoparticles Directed by a Zwitterionic Polymer"; DOI: 10.1002/chem.200601013; Chem. Eur. J. 2007, 13, 4197-4202; 2007 Wiley-VCH Verlag GmbH&Co. KGaA, Weinheim.
Ryouta Tatumi and Hisashi Fujihara; "Remarkably stable gold nanoparticles functionalized with a zwitterionic liquid based on imidazolium sulfonate in a high concentration of aqueous electrolyte and ionic liquid"; The Royal Society of Chemistry 2005; DOI: 10.1039/b413385d; Chem. Commun., 2005, 83-85.
Layal L. Rouhana, Jad A. Jaber, and Joseph B. Schlenoff; "Aggregation-Resistant Water-Soluble Gold Nanoparticles". In Final Form: Sep. 30, 2007; Langmuir 2007, 23, 12799-12801; Published on Web Nov. 16, 2007.
Kunihiko Kitadai, Masashi Takahashi, Masuo Takeda, Suresh K. Bhargava, Steven H. Priver and Martin A. Bennett; "Synthesis, structures and reactions of cyclometallated gold complexes containing (2-diphenylarsino-n-methyl)phenyl (n = 5, 6)"; DOI: 10.1039/b516538e; Dalton Trans., 2006, 2560-2571; The Royal Society of Chemistry 2006.
Pierre Starck, Wade K. J. Mosse, Nathan J. Nicholas, Marisa Spiniello, Johanna Tyrrell, Andrew Nelson, Greg G. Qiao and William A. Ducker; "Surface Chemistry and Rheology of Polysulfobetaine-Coated Silica". In Final Form: Apr. 26, 2007; 2007 American Chemical Society; Pages from 7587-7593; Published on Web Jun. 5, 2007.
Charles L. Mccormick and Andrew B. Lowe; "Aqueous RAFT Polymerization: Recent Developments in Synthesis of Functional Water-Soluble (Co)polymers with Controlled Structures"; Accounts of Chemical Research / vol. 37, No. 5, 2004; 2004 American Chemical Society; Acc. Chem. Res. 2004, 37, 312-325; Published on Web Mar. 13, 2004.
R. A. Salkar, P. Jeevanandam, G. Kataby, S. T. Aruna, Yuri Koltypin, O. Palchik and A. Gedanken; "Elongated Copper Nanoparticles Coated with a Zwitterionic Surfactant"; In Final Form: Aug. 16, 1999; 2000 American Chemical Society; J. Phys. Chem. B 2000, 104, 893-897; Published on Web Jan. 12, 2000.

* cited by examiner

*Primary Examiner* — Frederick Krass
*Assistant Examiner* — Isaac Shomer
(74) *Attorney, Agent, or Firm* — Paul J. DiConza (57) ABSTRACT

Compositions of nanoparticles functionalized with at least one zwitterionic moiety, methods for making a plurality of nanoparticles, and methods of their use as diagnostic agents are provided. The nanoparticles have characteristics that result in minimal retention of the particles in the body compared to other nanoparticles. The nanoparticle comprises a core, having a core surface essentially free of silica, and a shell attached to the core surface. The shell comprises at least one silane-functionalized zwitterionic moiety.

22 Claims, 6 Drawing Sheets

FIG. 1

Organic Acids

Carboxylic acids phosphonic acids

N-acylsulfonamides sulfonic acids monoalkylphosphonates imides sulfinic acids monoalkylphosphates tetrazoles Malonate derivatives dialkylphosphates aryl alcohols

Organic Bases

1°, 2°, 3°, 4° amines amidines guanidines pyridines pyrimidines pyrazines imidazoles pyrroles purines

FIG. 2

N,N-dimethyl-3-sulfo-N-(3-
(trimethoxysilyl)propyl)propan-1-aminium

3-(methyl(3-(trimethoxysilyl)propyl)amino)propane-1-
sulfonic acid 3-(3-(trimethoxysilyl)propylamino)propane-1-sulfonic acid 2-(2-(trimethylsilyl)ethoxy(hydroxy)phosphoryloxy)-
N,N,N-trimethylethanaminium 2-(2-(trimethoxysilyl)ethyl(hydroxy)phosphoryloxy)-
N,N,N-trimethylethanaminium

FIG. 3A

N,N,N-trimethyl-3-(N-3-(trimethoxysilyl)propionyl-sulfamoyl)propan-1-aminium N-((2H-tetrazol-5-yl)methyl)-N,N-dimethyl-3-(trimethoxysilyl)propan-1-aminium N-(2-carboxyethyl)-N,N-dimethyl-3-(trimethoxysilyl)propan-1-aminium 3-(methyl(3-(trimethoxysilyl)propyl)amino)propanoic acid

FIG. 3B

3-(3-(trimethoxysilyl)propylamino)propanoic acid

N-(carboxymethyl)-N,N-dimethyl-3-
(trimethoxysilyl)propan-1-aminium 2-(methyl(3-(trimethoxysilyl)propyl)amino)acetic acid 2-(3-(trimethoxysilyl)propylamino)acetic acid

FIG. 3C

2-(4-(3-(trimethoxysilyl)propylcarbamoyl)piperazin-1-yl)acetic acid 3-(4-(3-(trimethoxysilyl)propylcarbamoyl)piperazin-1-yl)propanoic acid 2-(methyl(2-(3-(trimethoxysilyl)propylureido)ethyl)amino)acetic acid 2-(2-(3-(trimethoxysilyl)propylureido)ethyl)aminoacetic acid

FIG. 3D

NANOPARTICLE CONTRAST AGENTS FOR DIAGNOSTIC IMAGING

BACKGROUND

This application relates generally to contrast agents for diagnostic imaging, such as for use in X-ray/Computed Tomography (CT) or Magnetic Resonance Imaging (MRI). More particularly, the application relates to nanoparticle-based contrast agents, and methods for making and using such agents.

Almost all clinically approved diagnostic contrast agents are small molecule based. Iodinated aromatic compounds have served as standard X-ray or CT contrast agents, while Gd-chelates are used for Magnetic Resonance Imaging. Although commonly used for diagnostic imaging, small molecule contrast agents may suffer from certain disadvantages such as leakage from blood vessel walls leading to short blood circulation time, lower sensitivity, high viscosity, and high osmolality. These compounds generally have been associated with renal complications in some patient populations. This class of small molecule agents is known to clear from the body rapidly, limiting the time over which they can be used to effectively image the vascular system as well as, in regards to other indications, making it difficult to target these agents to disease sites. Thus there is a need for a new class of contrast agents.

Nanoparticles are being widely studied for uses in medical applications, both diagnostic and therapeutic. While only a few nanoparticle-based agents have been clinically approved for magnetic resonance imaging applications and for drug delivery applications, hundreds of such agents are still in development. There is substantial evidence that nanoparticles have benefits over currently used small molecule-based agents in terms of efficacy for diagnostics and therapeutics. However, the effect of particle size, structure, and surface properties on the in-vivo bio-distribution and clearance of nanoparticle agents is not well understood. Nanoparticles, depending on their size, tend to stay in the body for longer periods compared to small molecules. In the case of contrast agents, it is preferred to have maximum renal clearance of the agents from the body without causing short term or long term toxicity to any organs.

In view of the above, there is a need for nanoparticle-based contrast agents or imaging agents with improved properties, particularly related to renal clearance and toxicity effects.

BRIEF DESCRIPTION OF THE INVENTION

The present invention provides a new class of nanoparticle-based contrast agents for X-ray, CT and MRI. The present inventors have found that nanoparticles functionalized with zwitterionic groups surprisingly have improved imaging characteristics compared to small molecule contrast agents. The nanoparticles of the present invention have characteristics that result in minimal retention of the particles in the body compared to other nanoparticles. These nanoparticles may provide improved performance and benefit in one or more of the following areas: robust synthesis, reduced cost, image contrast enhancement, increased blood half life, and decreased toxicity.

The present invention is directed to a composition comprising a nanoparticle, its method of making and method of use.

One aspect of the invention relates to a composition comprising a nanoparticle. The nanoparticle comprises a core, having a core surface essentially free of silica, and a shell attached to the core surface. The shell comprises at least one silane-functionalized zwitterionic moiety. In one embodiment, the core comprises a transition metal. In another embodiment, the core comprises a transition metal compound selected from the group consisting of oxides, carbides, sulfides, nitrides, phosphides, borides, halides, selenides, tellurides, or combinations thereof. In one embodiment, the core comprises a metal with an atomic number$\geq 34$.

In some embodiments, the composition comprises a nanoparticle comprising a tantalum oxide core, having a core surface essentially free of silica, and a shell attached to the core surface, wherein the shell comprises at least one silane-functionalized zwitterionic moiety. The nanoparticle has an average particle size up to about 6 nm.

In some other embodiments, the composition comprises a nanoparticle comprising a superparamagnetic iron oxide core, having a core surface essentially free of silica, and a shell attached to the core surface, wherein the shell comprises at least one silane-functionalized zwitterionic moiety. The nanoparticle has an average particle size up to about 50 nm.

In one or more embodiments, the invention relates to a diagnostic agent composition. The composition comprises a plurality of nanoparticles, wherein at least one nanoparticle of the plurality comprises a core, having a core surface essentially free of silica, and a shell attached to the core surface. The shell comprises at least one silane-functionalized zwitterionic moiety. In some embodiments, the composition further comprises a pharmaceutically acceptable carrier and optionally one or more excipients.

One aspect of the invention relates to methods for making a plurality of nanoparticles. The method comprises (a) providing a core, having a core surface essentially free of silica, and (b) disposing a shell attached to the core surface, wherein the shell comprises a silane-functionalized zwitterionic moiety.

Another aspect of the invention is directed to a method comprising administering a diagnostic agent composition to a subject and imaging the subject with an X-ray device. The diagnostic agent composition comprises a plurality of nanoparticles, wherein at least one nanoparticle of the plurality comprises a core and a shell. The shell comprises at least one silane-functionalized zwitterionic moiety. In one or more embodiments, the core comprises tantalum oxide.

In some embodiments, the method comprises administering a diagnostic agent composition to a subject, and imaging the subject with a diagnostic device. The diagnostic agent composition comprises a plurality of nanoparticles. At least one nanoparticle of the plurality comprises a core, having a core surface essentially free of silica, and a shell attached to the core surface. The shell comprises at least one silane-functionalized zwitterionic moiety. In one or more embodiments, the method further comprises monitoring delivery of the diagnostic agent composition to the subject with the diagnostic device and diagnosing the subject. In some embodiments, the diagnostic device employs an imaging method selected from the group consisting of magnetic resonance imaging, optical imaging, optical coherence tomography, X-ray, computed tomography, positron emission tomography, or combinations thereof.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The following detailed description is exemplary and is not intended to limit the invention of the application or the uses of the invention. Furthermore, there is no intention to be limited by any theory presented in the preceding background of the invention or the following detailed description.

In the following specification and the claims which follow, reference will be made to a number of terms having the following meanings. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts, while still being considered free of the modified term. For example, free of solvent or solvent-free, and like terms and phrases, may refer to an instance in which a significant portion, some, or all of the solvent has been removed from a solvated material.

Figure 1:
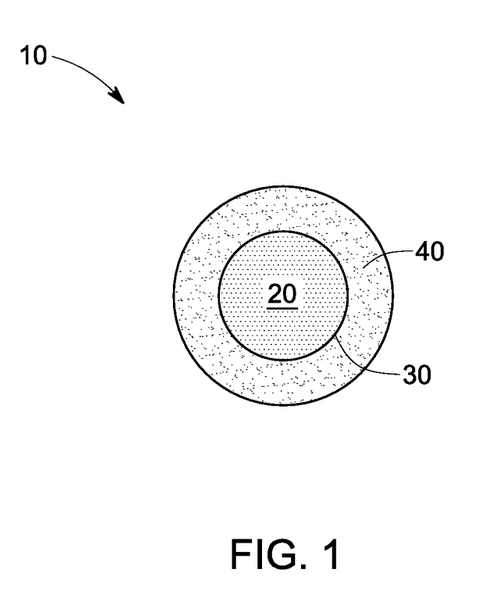
FIG. 1 depicts a cross-sectional view of a nanoparticle comprising a core and a shell, in accordance with some embodiments of the present invention.

One or more embodiments of the invention are related to a composition comprising a nanoparticle, as described in FIG. 1. The nanoparticle 10 composition comprises a core 20, having a core surface 30 essentially free of silica. In one or more embodiments, the core 20 contains a transition metal, for example, a compound of a transition metal element. The nanoparticle 10 further includes a shell 40, also referred to as a coating, attached to the core surface 30. The shell 40 comprises at least one silane-functionalized zwitterionic moiety. Because the core surface 30 is essentially free of silica, the silane-functionalized zwitterionic moieties are not bound to silica, but are bound to the core 20 at the core surface 30 without any intervening silica layer. The silane-functionalized zwitterionic moiety comprises a silane moiety and a zwitterionic moiety. As used herein, the term "zwitterionic moiety" refers to a moiety that is electrically neutral but carries formal positive and negative charges on different atoms. Zwitterions are polar and usually have a high solubility in water and a poor solubility in most organic solvents. In some embodiments, the "zwitterionic moiety" refers to a precursor to a zwitterionic moiety. In such embodiments, the precursor undergoes a secondary or subsequent chemical reaction to form a zwitterionic moiety.

"Nanoparticle" as used herein refers to particles having a particle size on the nanometer scale, generally less than 1 micrometer. In one embodiment, the nanoparticle has a particle size up to about 50 nm. In another embodiment, the nanoparticle has a particle size up to about 10 nm. In another embodiment, the nanoparticle has a particle size up to about 6 nm.

A plurality of nanoparticles may be characterized by one or more of median particle size, average diameter or particle size, particle size distribution, average particle surface area, particle shape, or particle cross-sectional geometry. Furthermore, a plurality of nanoparticles may have a distribution of particle sizes that may be characterized by both a number-average size and a weight-average particle size. The number-average particle size may be represented by $S_N = \Sigma(s_i n_i)/\Sigma n_i$, where $n_i$ is the number of particles having a particle size $s_i$. The weight average particle size may be represented by $S_W = \Sigma(s_i n_i^2)/\Sigma(s_i n_i)$. When all particles have the same size, $S_N$ and $S_W$ may be equal. In one embodiment, there may be a distribution of sizes, and $S_N$ may be different from $S_W$. The ratio of the weight average to the number average may be defined as the polydispersity index ($S_{PDI}$). In one embodiment, $S_{PDI}$ may be equal to about 1. In other embodiments, respectively, $S_{PDI}$ may be in a range of from about 1 to about 1.2, from about 1.2 to about 1.4, from about 1.4 to about 1.6, or from about 1.6 to about 2.0. In one embodiment, $S_{PDI}$ may be in a range that is greater than about 2.0.

In one embodiment, a plurality of nanoparticles may have a particle size distribution selected from a group consisting of normal distribution, monomodal distribution, and bimodal distribution. Certain particle size distributions may be useful to provide certain benefits. A monomodal distribution may refer to a distribution of particle sizes distributed about a single mode. In another embodiment, populations of particles having two distinct sub-population size ranges (a bimodal distribution) may be included in the composition.

A nanoparticle may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, a cube, or a whisker. A nanoparticle may include particles having two or more of the aforementioned shapes. In one embodiment, a cross-sectional geometry of the particle may be one or more of circular, ellipsoidal, triangular, rectangular, or polygonal. In one embodiment, a nanoparticle may consist essentially of non-spherical particles. For example, such particles may have the form of ellipsoids, which may have all three principal axes of differing lengths, or may be oblate or prelate ellipsoids of revolution. Non-spherical nanoparticles alternatively may be laminar in form, wherein laminar refers to particles in which the maximum dimension along one axis is substantially less than the maximum dimension along each of the other two axes. Non-spherical nanoparticles may also have the shape of frusta of pyramids or cones, or of elongated rods. In one embodiment, the nanoparticles may be irregular in shape. In one embodiment, a plurality of nanoparticles may consist essentially of spherical nanoparticles.

A population of nanoparticles may have a high surface-to-volume ratio. A nanoparticle may be crystalline or amorphous. In one embodiment, a single type (size, shape, and the like) of nanoparticle may be used, or mixtures of different types of nanoparticles may be used. If a mixture of nanoparticles is used they may be homogeneously or non-homogeneously distributed in the composition.

In one embodiment, the nanoparticle may be stable towards aggregate or agglomerate formation. An aggregate may include more than one nanoparticle in physical contact with one another, while agglomerates may include more than one aggregate in physical contact with one another. In some embodiments, the nanoparticles may not be strongly agglomerated and/or aggregated such that the particles may be relatively easily dispersed in the composition.

In one embodiment, the core comprises a transition metal. As used herein, "transition metal" refers to elements from groups 3-12 of the Periodic Table. In certain embodiments, the core comprises one or more transition metal compounds, such as oxides, carbides, sulfides, nitrides, phosphides, borides, halides, selenides, and tellurides, that contain one or more of these transition metal elements. Accordingly, in this description the term "metal" does not necessarily imply that a zero-valent metal is present; instead, the use of this term signifies the presence of a metallic or nonmetallic material that contains a transition metal element as a constituent.

In some embodiments, the nanoparticle may comprise a single core. In some other embodiments, the nanoparticle may comprise a plurality of cores. In embodiments where the nanoparticle comprises plurality of cores, the cores may be the same or different. In some embodiments, the nanoparticle composition comprises at least two cores. In other embodiments, each of the nanoparticle composition comprises only one core.

In some embodiments, the core comprises a single transition metal compound. In another embodiment, the core comprises two or more transition metal compounds. In embodiments where the core comprises two or more transition metal compounds, the transition metal element or the transition metal cation may be of the same element or of two or more different elements. For example, in one embodiment, the core may comprise a single metal compound, such as tantalum oxide or iron oxide. In another embodiment, the core may comprise two or more different metal elements, for example tantalum oxide and hafnium oxide or tantalum oxide and hafnium nitride, or oxides of iron and manganese. In another embodiment, the core may comprise two or more compounds of the same metal element, for example tantalum oxide and tantalum sulfide.

In one embodiment, the core creates a contrast enhancement in X-ray or computed tomography (CT) imaging. A conventional CT scanner uses a broad spectrum of X-ray energy between about 10 keV and about 150 keV. Those skilled in the art will recognize that the amount of X-ray attenuation passing through a particular material per unit length is expressed as the linear attenuation coefficient. At an X-ray energy spectrum typical in CT imaging, the attenuation of materials is dominated by the photoelectric absorption effect and the Compton Scattering effect. Furthermore, the linear attenuation coefficient is well known to be a function of the energy of the incident X-ray, the density of the material (related to molar concentration), and the atomic number (Z) of the material. For molecular compounds or mixtures of different atoms the 'effective atomic number,' $Z_{eff}$, can be calculated as a function of the atomic number of the constituent elements. The effective atomic number of a compound of known chemical formula is determined from the relationship:

$$Z_{eff} = \left[\sum_{k=1}^{P} w_{f_k} Z_k^{\beta}\right]^{1/\beta} \quad \text{(Eq. 1)}$$

where $Z_k$ is the atomic number of metal elements, P is the total quantity of metal elements, and $w_{f_k}$ is the weight fraction of metal elements with respect to the total molecular weight of the molecule (related to the molar concentration). The optimal choice of the incident X-ray energy for CT imaging is a function of the size of the object to be imaged and is not expected to vary much from the nominal values. It is also well known that the linear attenuation coefficient of the contrast agent material is linearly dependent on the density of the material, i.e., the linear attenuation coefficient can be increased if the material density is increased or if the molar concentration of the contrast material is increased. However, the practical aspects of injecting contrast agent material into patients, and the associated toxicity effects, limit the molar concentration that can be achieved. Therefore it is reasonable to separate potential contrast agent materials according to their effective atomic number. Based on simulations of the CT contrast enhancement of typical materials for a typical CT energy spectrum with a molar concentration of approximately 50 mM, it is estimated that materials with effective atomic number greater than or equal to 34 may yield appropriate contrast enhancement of about 30 Hounsfield units (HU), or 3% higher contrast than water. Therefore, in certain embodiments the core comprises material having an effective atomic number greater than or equal to 34. See, e.g., Chapter 1 in Handbook of Medical Imaging, Volume 1. Physics and Psychophysics, Eds. J. Beutel, H. L. Kundel, R. L. Van Metter, SPIE Press, 2000.

A core that contains transition metals with relatively high atomic number as described above may provide embodiments having certain desirable characteristics. In such embodiments, the core is substantially radiopaque, meaning that the core material prohibits significantly less X-ray radiation to pass through than materials typically found in living organisms, thus potentially giving the particles utility as contrast agents in X-ray imaging applications, such as computed tomography (CT). Examples of transition metal elements that may provide this property include tungsten, tantalum, hafnium, zirconium, molybdenum, silver, and zinc. Tantalum oxide is one particular example of a suitable core composition for use in X-ray imaging applications. In one or more embodiments, the core of the nanoparticle comprises tantalum oxide and the nanoparticle has a particle size up to about 6 nm. This embodiment may be particularly attractive for applications in imaging techniques that apply X-rays to generate imaging data, due to the high degree of radiopacity of the tantalum-containing core and the small size that aids rapid renal clearance, for example.

In some embodiments, the core of the nanoparticle comprises at least about 30% transition metal material by weight. In certain embodiments, the core comprises at least about 50% transition metal material by weight. In still further embodiments, the core comprises at least about 75% transition metal material by weight. Having a high transition metal material content in the core provides the nanoparticle with higher degree of radiopacity per unit volume, thereby imparting more efficient performance as an contrast agent.

In another embodiment, the core comprises material that exhibits magnetic behavior, including, for example, superparamagnetic behavior. The "superparamagnetic material" as used herein refers to material that may exhibit a behavior similar to paramagnetism even when at temperatures below the Curie or the Néel temperature. Examples of potential magnetic or superparamagnetic materials include materials comprising one or more of iron, manganese, copper, cobalt, or nickel. In one embodiment, the superparamagnetic material comprises superparamagnetic iron oxide. In some embodiments, the nanoparticles of the present invention may be used as magnetic resonance (MR) contrast agents. These nanoparticles may yield a T2*, T2, or T1 magnetic resonance signal upon exposure to a magnetic field. In one or more embodiments, the core of the nanoparticle comprises superparamagnetic iron oxide and the nanoparticle has a particle size up to about 50 nm.

In one embodiment, the nanoparticle 10 comprises a shell 40 substantially covering the core 20. This shell 40 may serve to stabilize the core 20, i.e., the shell 40 may prevent one core 20 from contacting an adjacent core 20, thereby preventing a plurality of such nanoparticle 10 from aggregating or agglomerating as described herein, or by preventing leaching of metal or metal oxide, for instance, on the time scale of in-vivo imaging experiments. In one embodiment, the shell 40 may be of a sufficient thickness to stabilize the core 20 and prevent such contact. In one embodiment, the shell 40 has an average thickness up to about 50 nm. In another embodiment, the shell 40 has an average thickness up to about 3 nm.

As used herein, the term "substantially covering" means that a percentage surface coverage of the nanoparticle is greater than about 20%. Percentage surface coverage refers to the ratio of nanoparticle surface covered by the shell to the surface area not covered by the shell. In some embodiments, the percentage surface coverage of the nanoparticle may be greater than about 40%.

In some embodiments, the shell may facilitate improved water solubility, reduce aggregate formation, reduce agglomerate formation, prevent oxidation of nanoparticles, maintain the uniformity of the core-shell entity, or provide biocompatibility for the nanoparticles. In another embodiment, the material or materials comprising the shell may further comprise other materials that are tailored for a particular application, such as, but not limited to, diagnostic applications. For instance, in one embodiment, the nanoparticle may further be functionalized with a targeting ligand. The targeting ligand may be a molecule or a structure that provides targeting of the nanoparticle to a desired organ, tissue or cell. The targeting ligand may include, but is not limited to, proteins, peptides, antibodies, nucleic acids, sugar derivatives, or combinations thereof. In some embodiments, the nanoparticle further comprises targeting agents such that, when used as contrast agents, the particles can be targeted to specific diseased areas of the subject's body. In some embodiments, the nanoparticles may be used as blood pool agents.

The cores may be covered with one or more shells. In some embodiments, a plurality of cores may be covered with the same shell. In one embodiment, a single shell may cover all the cores present in the nanoparticle composition. In some embodiments, the individual cores may be covered with one or more shells. In another embodiment, all the cores present in the nanoparticle may be covered with two or more shells. An individual shell may comprise the same material or may comprise two or more different materials. In embodiments where the core may be covered with more than one shell, the shell may be of the same or of different material.

In one embodiment, the shell comprises at least one silane-functionalized zwitterionic moiety, wherein the silane-functionalized zwitterionic moiety comprises a silane moiety and a zwitterionic moiety. In some embodiments, the silane moiety of the silane-functionalized zwitterionic shell is directly attached to the core.

In one embodiment, the shell comprises a plurality of silane moieties, wherein at least one of the plurality of silane moieties is functionalized with at least one zwitterionic moiety. In some embodiments, the shell comprises silane-functionalized zwitterionic moieties and silane-functionalized non-zwitterionic moieties. In such embodiments, a ratio of silane-functionalized zwitterionic moieties to silane-functionalized non-zwitterionic moieties is from about 0.01 to about 100. In some other embodiments, the ratio of silane-functionalized zwitterionic moieties to silane-functionalized non-zwitterionic moieties is from about 0.1 to about 20.

In some embodiments, the shell comprises a plurality of silane-functionalized zwitterionic moieties. The term "plurality of silane-functionalized zwitterionic moieties" refers multiple instances of one particular silane moiety, functionalized with at least one zwitterionic moiety. The silane moieties may be the same or different. In one embodiment, each core is surrounded by a plurality of silane-functionalized zwitterionic moieties, wherein all the silane moieties are of the same type. In another embodiment, each core is surrounded by a plurality of silane-functionalized zwitterionic moieties, wherein the silane moieties are of different types. In one embodiment, each of the plurality of silane moieties is functionalized with at least one zwitterionic moiety. In one embodiment, at least one of the plurality of silane moieties is functionalized with a zwitterionic moiety such that each nanoparticle, on average, comprises at least one zwitterionic moiety. In one or more embodiments, each nanoparticle comprises a plurality of zwitterionic moieties.

In embodiments wherein the shell comprises a plurality of silane-functionalized zwitterionic moieties, the silane moieties and the zwitterionic moieties may be the same or different. For example, in one embodiment, all the silane moieties may be the same and all the zwitterionic moieties may be the same. In another embodiment, the silane moieties are the same but the zwitterionic moieties are different. For example, the shell may comprise two different silane-functionalized zwitterionic moieties. The first one comprises a type 1 silane moiety and a type 1 zwitterionic moiety. The second one comprises a type 1 silane moiety and a type 2 zwitterionic moiety, or a type 2 silane moiety but a type 1 zwitterionic moiety, or a type 2 silane moiety and a type 2 zwitterionic moiety. In one or more embodiments, the silane-functionalized zwitterionic moiety may comprise two or more zwitterionic moieties. In embodiments where the silane-functionalized zwitterionic moiety comprises two or more zwitterionic moieties, the zwitterionic moieties may be the same or different.

Figure 2:
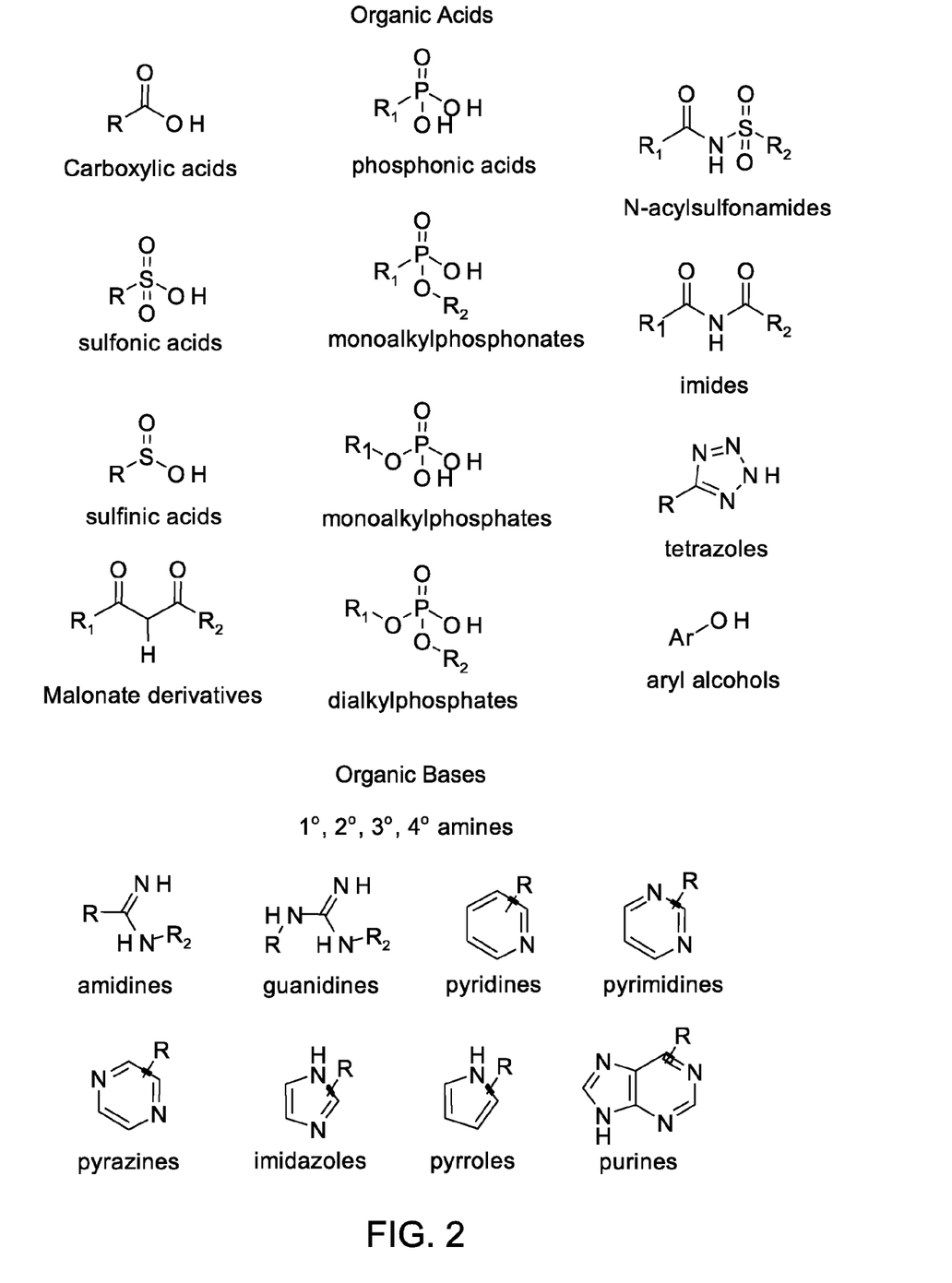
FIG. 2 describes organic acids and organic bases from which the zwitterionic functional groups may be formed.
Figure 3A:
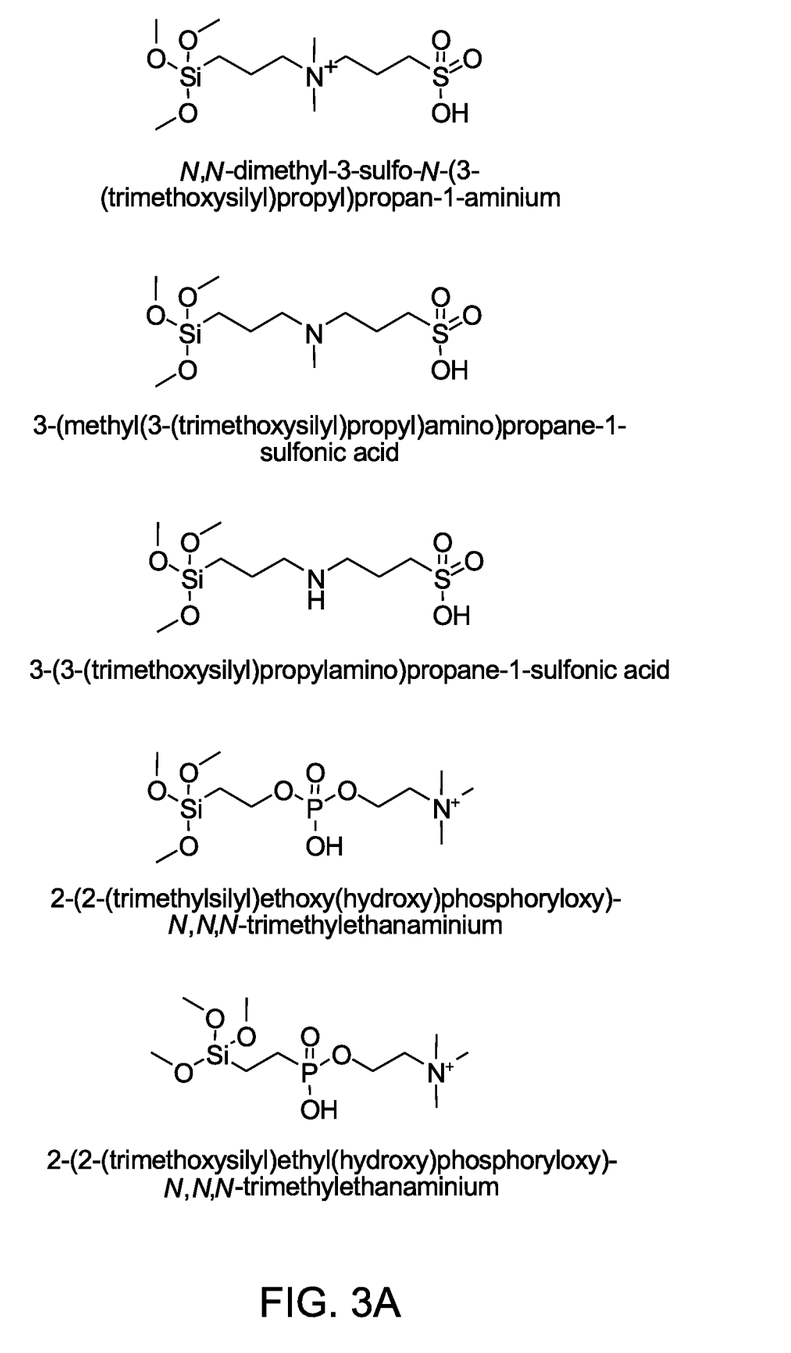
FIGS. 3A, 3B, 3C and 3D describe silane-functionalized zwitterionic moieties, which may react with the core to produce a shell comprising silane functional zwitterionic moieties.
Figure 3B:
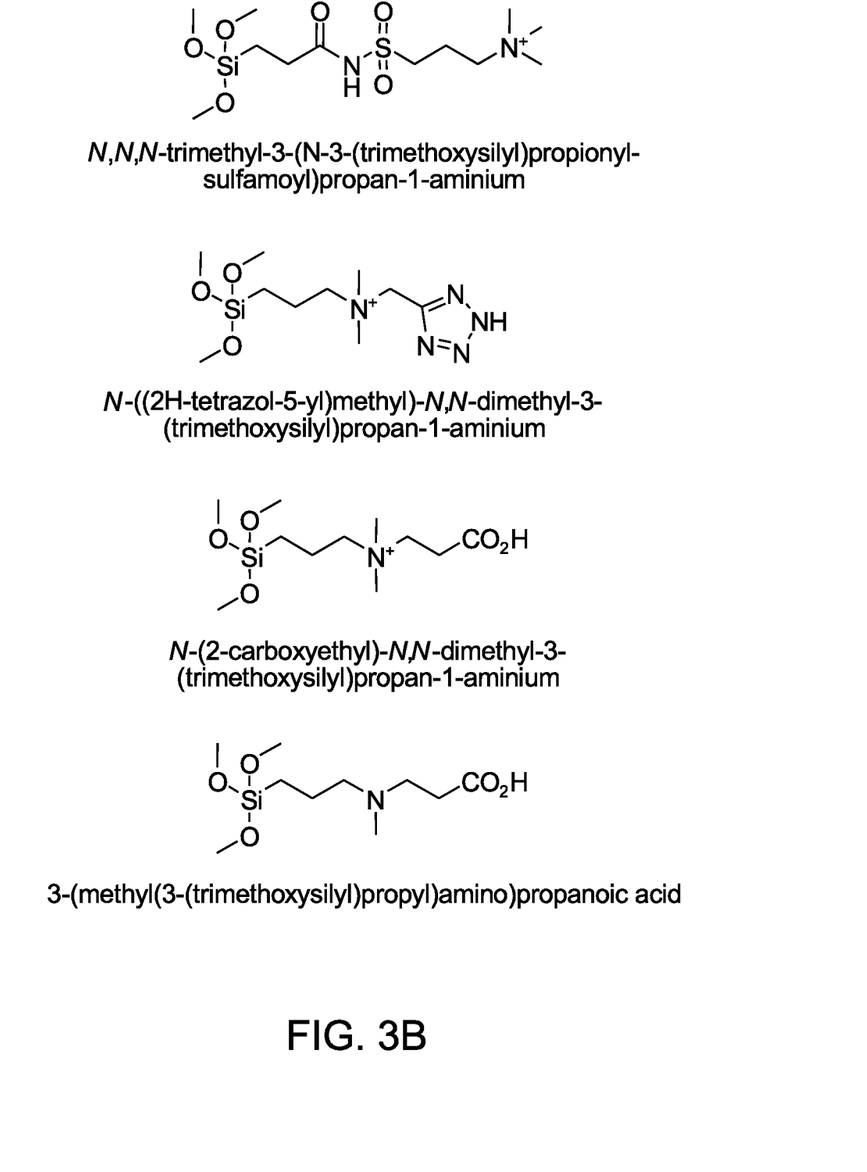
Figure 3C:
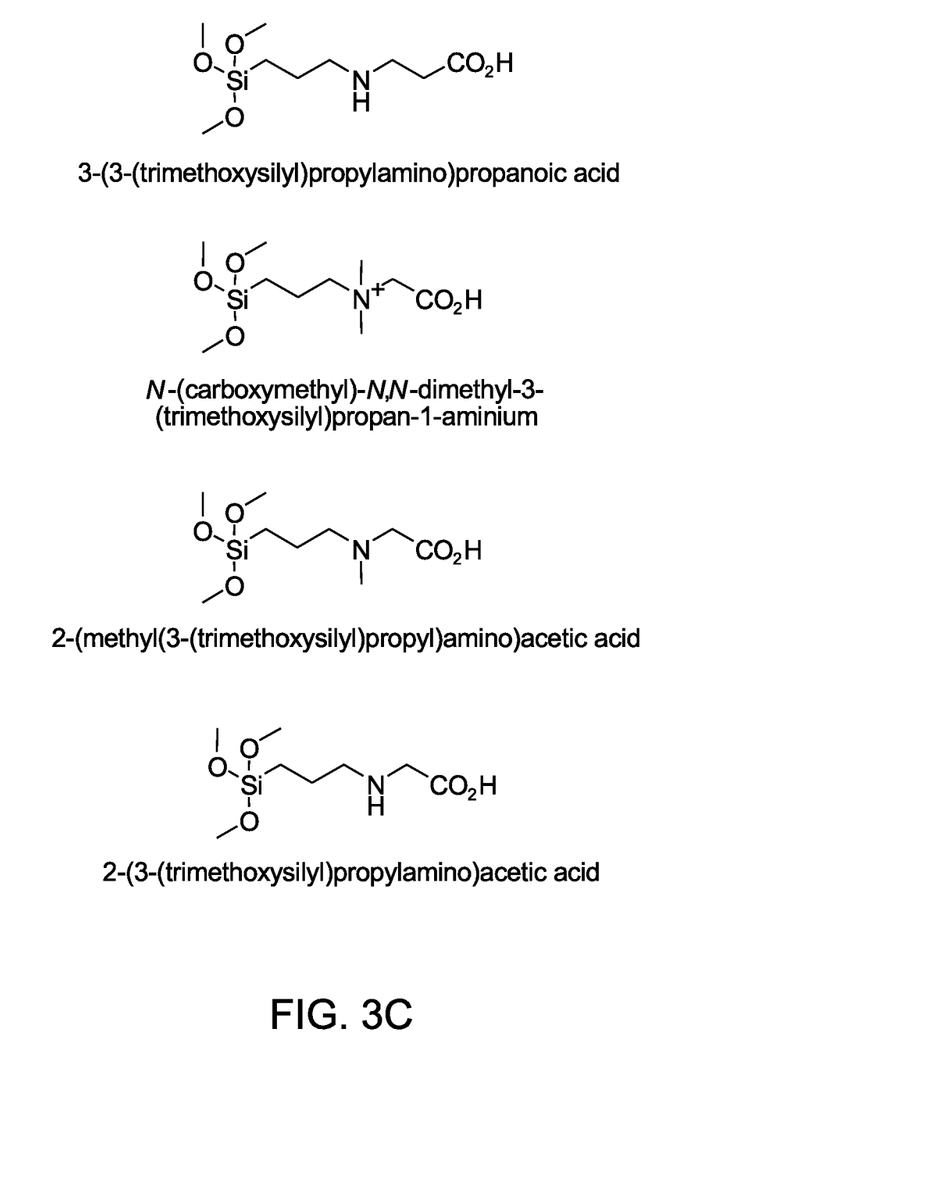
Figure 3D:
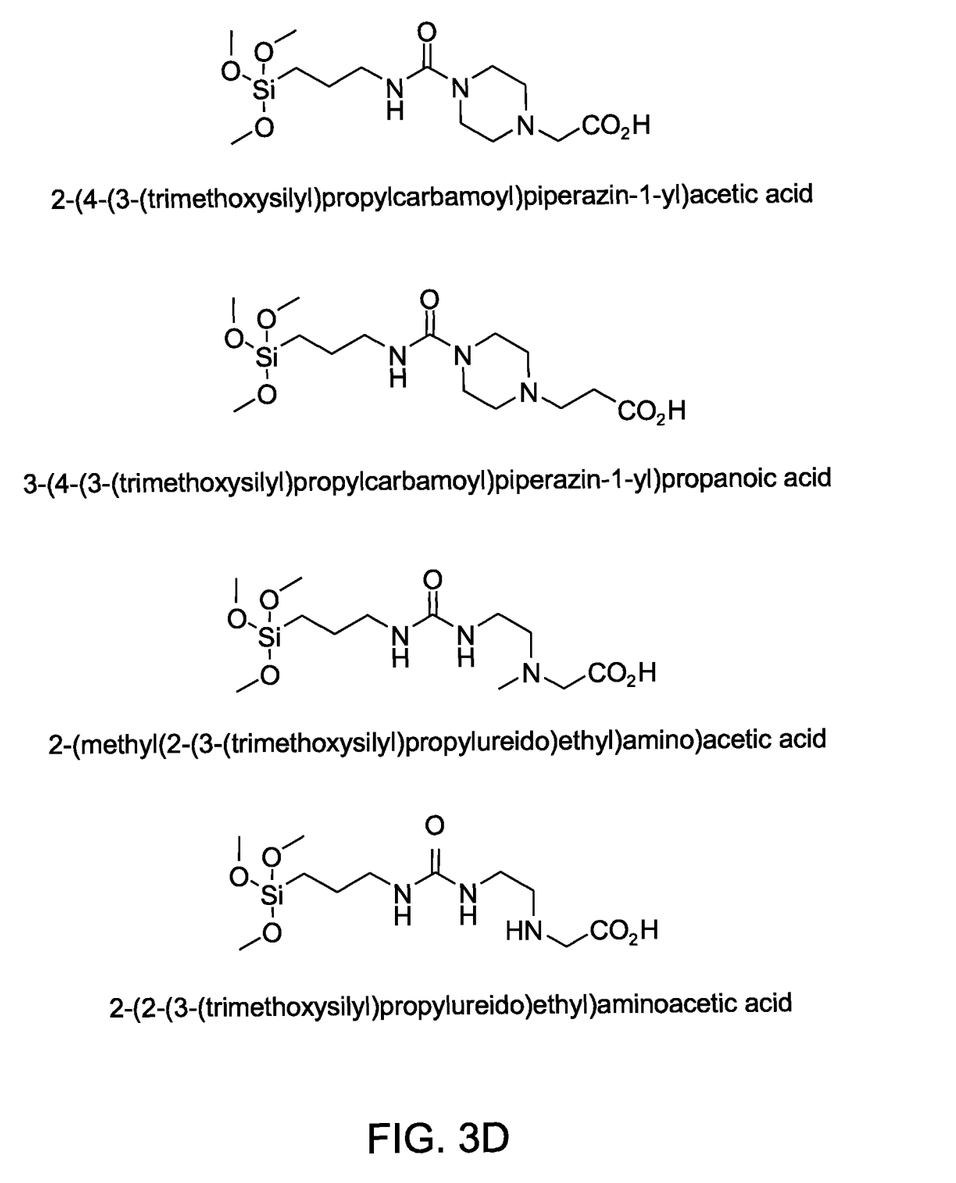

In some embodiments, the silane-functionalized zwitterionic moiety comprises a positively charged moiety, a negatively charged moiety and a first spacer group in between the positively charged moiety and the negatively charged moiety. The positively charged moiety may originate from organic bases and the negatively charged moiety may originate from organic acids. FIG. 2 presents a list of exemplary organic acids and bases from which the negatively charged moiety and the positively charged moiety may originate.

In some embodiments, the positively charged moiety comprises protonated primary amines, protonated secondary amines, protonated tertiary alkyl amines, protonated amidines, protonated guanidines, protonated pyridines, protonated pyrimidines, protonated pyrazines, protonated purines, protonated imidazoles, protonated pyrroles, quaternary alkyl amines, or combinations thereof.

In some embodiments, the negatively charged moiety comprises deprotonated carboxylic acids, deprotonated sulfonic acids, deprotonated sulfinic acids, deprotonated phosphonic acids, deprotonated phosphoric acids, deprotonated phosphinic acids, or combinations thereof.

In one or more embodiments, the first spacer group comprises alkyl groups, aryl groups, substituted alkyl and aryl groups, heteroalkyl groups, heteroaryl groups, carboxy groups, ethers, amides, esters, carbamates, ureas, straight chain alkyl groups of 1 to 10 carbon atoms in length, or combinations thereof.

In some embodiments, a silicon atom of the silane-functionalized zwitterionic moiety is connected to the positively or negatively charged moiety via a second spacer group. In some embodiments, the second spacer group comprises alkyl groups, aryl groups, substituted alkyl and aryl groups, heteroalkyl groups, heteroaryl groups, carboxy groups, ethers, amides, esters, carbamates, ureas, straight chain alkyl groups of 1 to 10 carbon atoms in length, or combinations thereof.

In some embodiments, the silane-functionalized zwitterionic moiety comprises the hydrolysis product of a precursor tri-alkoxy silane, such as those illustrated in FIG. 3A-3D. In some embodiments, the precursor tri-alkoxy silane comprises N,N-dimethyl-3-sulfo-N-(3-(trimethoxysilyl)propyl)propan-1-aminium, 3-(methyl(3-(trimethoxysilyl)propyl) amino) propane-1-sulfonic acid, 3-(3-(trimethoxysilyl)propylamino) propane-1-sulfonic acid, 2-(2-(trimethylsilyl) ethoxy(hydroxy) phosphoryloxy)-N,N,N-trimethylethanaminium, 2-(2-(trimethoxysilyl)ethyl (hydroxy)phosphoryloxy)-N,N,N-trimethylethanaminium, N,N,N-trimethyl-3-(N-3-(trimethoxysilyl) propionylsulfamoyl)propan-1-aminium, N-((2H-tetrazol-5-yl)methyl)-N, N-dimethyl-3-(trimethoxysilyl)propan-1-aminium, N-(2-carboxyethyl)-N,N-dimethyl-3-(trimethoxysilyl)propan-1-aminium, 3-(methyl(3-(trimethoxysilyl)propyl)amino) propanoic acid, 3-(3-(trimethoxysilyl)propylamino) propanoic acid, N-(carboxymethyl)-N,N-dimethyl-3-(trimethoxysilyl)propan-1-aminium, 2-(methyl(3-(trimethoxysilyl)propyl)amino)acetic acid, 2-(3-(trimethoxysilyl)propylamino)acetic acid, 2-(4-(3-(trimethoxysilyl) propylcarbamoyl)piperazin-1-yl)acetic acid, 3-(4-(3-(trimethoxysilyl)propylcarbamoyl)piperazin-1-yl)propanoic acid, 2-(methyl(2-(3-(trimethoxysilyl)propylureido)ethyl) amino)acetic acid, 2-(2-(3-(trimethoxysilyl)propylureido) ethyl)aminoacetic acid, or combinations thereof.

Another aspect of the invention relates to a diagnostic agent composition. The diagnostic agent composition comprises a plurality of the nanoparticles 10 described previously. In one embodiment, the diagnostic agent composition further comprises a pharmaceutically acceptable carrier and optionally one or more excipients. In one embodiment, the pharmaceutically acceptable carrier may be substantially water. Optional excipients may comprise one or more of salts disintegrators, binders, fillers, or lubricants.

A small particle size may be advantageous in facilitating clearance from kidneys and other organs, for example. In one embodiment, the plurality of nanoparticles may have a median particle size up to about 50 nm. In another embodiment, the plurality of nanoparticles may have a median particle size up to about 10 nm. In another embodiment, the plurality of nanoparticles may have a median particle size up to about 6 nm.

One aspect of the invention relates to methods for making a plurality of nanoparticles. In general, one method comprises (a) providing a core having a core surface essentially free of silica, and (b) disposing a shell attached to the core surface, wherein the shell comprises a silane-functionalized zwitterionic moiety.

In one or more embodiments, the step of providing a core comprises providing a first precursor material, wherein the first precursor material comprises at least one transition metal. In one embodiment, the first precursor material reacts to generate the core comprising at least one transition metal. In one embodiment, the first precursor material decomposes to generate the core. In another embodiment, the first precursor material hydrolyses to generate the core. In another embodiment, the first precursor material reacts to form the core. Nanoparticle synthesis methods are well known in the art and any suitable method for making a nanoparticle core of an appropriate material may be suitable for use in this method.

In one or more embodiments, the step of disposing a shell comprises providing a second precursor material, such as a material comprising a silane moiety or a precursor to a silane moiety. The silane moiety may react with the core to form a shell comprising a silane moiety. In some embodiments, the precursor may undergo a hydrolysis reaction before reacting with the core. In some embodiments, the silane moiety may be functionalized with at least one zwitterionic moiety or at least one precursor to a zwitterionic moiety. In embodiments wherein the silane moiety is functionalized with at least one zwitterionic moiety, the shell, thus formed, comprises a silane-functionalized zwitterionic moiety. In embodiments wherein the silane moiety is functionalized with a precursor to a zwitterionic moiety, the shell, thus produced, may not be zwitterionic in nature, but may subsequently react with an appropriate reagent to convert the precursor into a zwitterionic moiety. In one or more embodiments, the second precursor material comprises the silane-functionalized zwitterionic moiety or precursor to a silane-functionalized zwitterionic moiety, such as one or more of the precursor tri-alkoxy silanes described above.

It will be understood that the order and/or combination of steps may be varied. Thus, according to some embodiments, steps (a) and (b) occur as sequential steps so as to form the nanoparticle from the core and the second precursor material. By way of example and not limitation, in some embodiments, the first precursor material comprises at least one transition metal; wherein the core comprises an oxide of the at least one transition metal; and step (a) further comprises hydrolysis of the first precursor material. According to some embodiments, the first precursor material is an alkoxide or halide of the transition metal, and the hydrolysis process includes combining the first precursor material with an acid and water in an alcoholic solvent. In some embodiments, the silane may comprise polymerizable groups. The polymerization may proceed via acid catalyzed condensation polymerization. In some other embodiments, the silane moiety may be physically adsorbed on the core. In some embodiments, the silane moiety may be further functionalized with other polymers. The polymer may be water soluble and biocompatible. In one embodiment, the polymers include, but are not limited to, polyethylene glycol (PEG), polyethylene imine (PEI), polymethacrylate, polyvinylsulfate, polyvinylpyrrolidinone, or combinations thereof.

In some embodiments, the core comprises metal oxides. In one embodiment, the metal oxide core may be synthesized upon the hydrolysis of a metal alkoxide in the presence of an organic acid. In some embodiments, the metal alkoxide may be a tantalum alkoxide such as tantalum ethoxide, the organic acid may be a carboxylic acid such as isobutyric acid, propionic acid or acetic acid and the hydrolysis reaction may be carried out in the presence of an alcohol solvent such as 1-propanol or methanol.

In another embodiment, the core and the second precursor material may be brought into contact to each other. In one embodiment, the second precursor material may comprise a silicon containing species such as an organofunctional tri-alkoxysilane or mixture of organofunctional tri-alkoxysilanes. At least one of the organofunctional tri-alkoxy silanes may contain at least one zwitterionic group or a precursor to a zwitterionic group, such that each nanoparticle, on average, may contain at least one zwitterionic moiety or precursor to a zwitterionic moiety. In one embodiment, each nanoparticle may contain on average, a plurality of zwitterionic moieties or precursors to zwitterionic moieties. In other embodiments, the core may be treated with a mixture containing at least two silane moieties. In one embodiment, one silane moiety is functionalized with a zwitterionic moiety, or a precursor to a zwitterionic moiety, and the second silane moiety may not be functionalized with any zwitterionic moiety. The charged silane moieties may be added simultaneously or sequentially. In some embodiments, one or more silane moieties functionalized with a zwitterionic moiety, or with a precursor to a zwitterionic moiety, may be added to the cores functionalized with non-zwitterionic silane moieties, either simultaneously or sequentially.

In one embodiment, a tantalum oxide core may be allowed to react with an alkoxy silane that contains both, a quaternary nitrogen as well as a sulfonate group or a carboxy group, for example, a sulfobetaine group or a betaine group. In one embodiment the tantalum oxide core may be allowed to react with $(RO)_3Si(CH_2)_xNR'_2(CH_2)_ySO_3$, where R is an alkyl or aryl group, x is 1-10, y is 1-10, and R' is H, an alkyl group or an aryl group. In one embodiment, the R is an alkyl group, such as methyl or ethyl, x is 3, y is between 2-5, and R' is H or an alkyl group such as methyl.

In one embodiment, sulfobetaine-functionalized silanes may be synthesised upon the ring opening reaction of alkyl sultones or a mixture of alkyl sultones with amine substituted silanes. In another embodiment, alkyl lactones or mixtures of alkyl lactones may be used in place of the alkyl sultones. In certain embodiments, the shell comprises a mixture of sulfobetaine and betaine functional silanes. In another embodiment, the metal oxide core may react with a sulfobetaine or betaine functional silane moiety, in which the sulfonate or carboxy group may be chemically protected.

In another embodiment, the tantalum oxide core may be allowed to react with an amine-containing silane, such as an amino-functional trialkoxysilane, to form a tantalum oxide core functionalized with the amine-containing silane. In a second step, the core functionalized with the silane may be isolated. In an alternative embodiment, the core functionalized with the silane may be used in-situ. The core functionalized with the silane may be allowed to react with an alkyl sultone, an alkyl lactone, a haloalkylcarboxylic acid or ester, mixtures of alkyl sultones, mixtures of alkyl lactones, mixtures of haloalkylcarboxylic acids or esters, or mixtures of both alkyl sultones and alkyl lactones to form a zwitterionic moiety. The amount of sultone, lactone or mixture of sultones and/or lactones may be sufficient to provide, on average, at least one zwitterionic moiety per nanoparticle. Non-limiting examples of alkyl sultones include propane sultone and butyl sultone. Non-limiting examples of lactones include propane lactone and butyl lactone.

In one embodiment, the method further comprises fractionating the plurality of nanoparticles. The fractionating step may include filtering the nanoparticles. In another embodiment, the method may further comprise purifying the plurality of nanoparticles. The purification step may include use of dialysis, tangential flow filtration, diafiltration, or combinations thereof. In another embodiment, the method further comprises isolation of the purified nanoparticles.

In combination with any of the above-described embodiments, some embodiments relate to a method for making a diagnostic agent composition for X-ray/computed tomography or MRI. The diagnostic agent composition comprises a plurality of nanoparticles. In some embodiments, the median particle size of the plurality of nanoparticles may not be more than about 10 nm, for example not more than about 7 nm, and in particular embodiments not more than about 6 nm. It will be understood that according to some embodiments, the particle size of the plurality of nanoparticles may be selected so as to render the nanoparticle substantially clearable by a mammalian kidney, such as a human kidney, in particulate form.

In some embodiments, the present invention is directed to a method of use of the diagnostic agent composition comprising a plurality of the nanoparticles described herein. In some embodiments, the method comprises the in-vivo or in-vitro administration of the diagnostic agent composition to a subject, which in some instances may be a live subject, such as a mammal, and subsequent image generation of the subject with an X-ray/CT device. The nanoparticles, as described above, comprise a core and a shell, wherein the shell comprises at least one silane-functionalized zwitterionic moiety. In one embodiment, the core comprises tantalum oxide. The nanoparticle may be introduced to the subject by a variety of known methods. Non-limiting examples for introducing the nanoparticle to the subject include intravenous, intra-arterial or oral administration, dermal application, or direct injection into muscle, skin, the peritoneal cavity or other tissues or bodily compartments.

In another embodiment, the method comprises administering the diagnostic agent composition to a subject, and imaging the subject with a diagnostic device. The diagnostic device employs an imaging method, examples of which include, but are not limited to, MRI, optical imaging, optical coherence tomography, X-ray, computed tomography, positron emission tomography, or combinations thereof. The diagnostic agent composition, as described above, comprises a plurality of the nanoparticles 10.

In one embodiment, the methods described above for use of the diagnostic contrast agent further comprise monitoring delivery of the diagnostic agent composition to the subject with the diagnostic device, and diagnosing the subject; in this method data may be compiled and analyzed generally in keeping with common operation of medical diagnostic imaging equipment. The diagnostic agent composition may be an X-ray or CT contrast agent, for example, such as a composition comprising a tantalum oxide core. The diagnosing agent composition may provide for a CT signal in a range from about 100 Hounsfield to about 5000 Hounsfield units. In another example, the diagnostic agent composition may be a MRI contrast agent, such as an agent comprising a superparamagnetic iron oxide core.

One embodiment of the invention provides a method for determination of the extent to which the nanoparticles 10 described herein, such as nanoparticles having tantalum oxide or iron oxide cores, are distributed within a subject. The subject may be a mammal or a biological material comprising a tissue sample or a cell. The method may be an in-vivo or in-vitro method. The nanoparticle may be introduced to the subject by a variety of known methods. Non-limiting examples for introducing the nanoparticle to the subject include any of the known methods described above. In one embodiment, the method comprises (a) introducing the nanoparticles into the subject, and (b) determining the distribution of the nanoparticles in the subject. Distribution within a subject may be determined using a diagnostic imaging technique such as those mentioned previously. Alternatively, the distribution of the nanoparticle in the biological material may be determined by elemental analysis. In one embodiment, Inductively Coupled Plasma Mass Spectroscopy (ICP-MS) may be used to determine the concentration of the nanoparticle in the biological material.

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLES

Practice of the invention will be still more fully understood from the following examples, which are presented herein for illustration only and should not be construed as limiting the invention in any way.

The abbreviations used in the examples section are expanded as follows: "mg": milligrams; "mL": milliliters; "mg/mL": milligrams per milliliter; "mmol": millimoles; "µL" and µLs: microliters "LC": Liquid Chromatography; "DLS": Dynamic Light Scattering; "DI": Deionized water, "ICP": Inductively Coupled Plasma.

Unless otherwise noted, all reagent-grade chemicals were used as received, and Millipore water was used in the preparation of all aqueous solutions.

Synthesis of Tantalum Oxide-Based Nanoparticles

Step-1: Synthesis of N,N-dimethyl-3-sulfo-N-(3-(trimethoxysilyl)propyl)propan-1-aminium Toluene (anhydrous, 250 mL), N,N-dimethylaminotrimethoxysilane (25 g, 121 mmol) and 1,3-propane sultone (13.4 g, 110 mmol) were added to a 500 mL round bottom flask containing a stir bar. The mixture was stirred at room temperature for 4 days. The mixture was then filtered to isolate the precipitated product, which was subsequently washed with fresh anhydrous toluene (2×60 mL). The yield of white powder after drying under vacuum was 23.6 g.

Step-2: Reaction of N,N-dimethyl-3-sulfo-N-(3-(trimethoxysilyl)propyl)propan-1-aminium with Tantalum Oxide Based Core Method-1: 1-propanol as Solvent A 250 mL three necked round bottomed flask containing a stir bar was charged with 1-propanol (73 mL), followed by addition of isobutyric acid (1.16 mL, 12.51 mmol, 1.27 eq with respect to Ta) and DI water (1.08 mL, 59.95 mmol, 6.09 eq with respect to Ta) to form a reaction mixture. Nitrogen was bubbled through the reaction mixture for 20 minutes followed by dropwise addition of tantalum ethoxide (Ta(OEt)$_5$) (2.55 mL, 4 g, 9.84 mmol) to the reaction mixture at room temperature with stirring over 15 minutes. During the addition of Ta(OEt)$_5$, the nitrogen was continued to bubble through the reaction mixture. The above mentioned reaction mixture was allowed to stir at room temperature under nitrogen for 16 hours after the Ta(OEt)$_5$ addition was complete.

The reaction mixture was stirred at room temperature for 16 hours and then an aliquot (1.5 mL) was taken out from the reaction mixture, filtered through a 20 nm filtration membrane, and the particle size was measured (as the hydrodynamic radius) in water by DLS immediately after the filtration step. The average particle size was measured to be approximately 3.6 nm. N,N-dimethyl-3-sulfo-N-(3-(trimethoxysilyl)propyl)propan-1-aminium (4.03 g, 12.23 mmol, 1.24 eq with respect to Ta) was dissolved in 50 mL of DI water. This solution was added to the above mentioned reaction mixture dropwise over a few minutes. The colorless, homogeneous reaction mixture was changed immediately into a cloudy white solution and finally became a milky solution by the end of the addition of the silane-functionalized zwitterionic moiety. After the addition was complete a condenser was attached to the flask, and the reaction mixture was kept under a nitrogen blanket. The flask was placed in an oil bath preheated to 75° C. and the reaction mixture was stirred for 6 hours. The reaction mixture became clearer. After 6 hours, the reaction mixture was cooled to room temperature under a blanket of air. The heterogeneous reaction mixture was neutralized to pH 6-7 using 1(M) NH$_4$OH. The reaction mixture was transferred into a second round bottom flask under a blanket of air. During the transfer of the reaction mixture to the second flask, an amount of white material remained in the flask, and did not get transferred to the second flask (crude product A). This crude product A was dried under a flow of nitrogen overnight. Meanwhile, the solution of the second flask was evaporated using a rotary evaporator at 50° C. The dry white residue obtained after the evaporation of the solution, (crude product B) was allowed to stand under a nitrogen flow over night.

The crude product A was dried overnight. This solid was completely dissolved in DI water. Crude product B was also completely dissolved in DI water, and the two solutions (crude product A & crude product B) were combined (total volume was 60 mL). The aqueous solution was filtered sequentially through 450 nm, 200 nm and 100 nm filtration membranes and finally through a 20 nm filtration membrane. The solution was then first dialyzed at pH 7.0 using sodium phosphate buffer (10K molecular weight cut-off snakeskin regenerated cellulose tubing), and then three times in DI water.

Finally, the nanoparticle was isolated by lyophilization. Yield of white powder=1.748 g (38% yield based on Ta). Zeta potential: (−)8.18 mV. Elemental analysis: 38.3±0.3% Ta, 4.8±0.1% Si. The average particle size was measured to be 8.9 nm by DLS. Purity of the nanoparticle was measured by Liquid Chromatography (LC)/Inductively Coupled Plasma (ICP).

Method-2: Trifluoroethanol as Solvent

A 100 mL three necked round bottom flask containing a stir bar was charged with trifluoroethanol (42 mL). While the solvent was sparged with nitrogen, isobutyric acid (0.53 mL, 5.7 mmol) followed by water (0.13 mL, 7.4 mmol) were added using a syringe. The solution was allowed to stir for an additional 15 min with continuous nitrogen bubbling. Tantalum ethoxide (Ta(OEt)$_5$) (2 g, 4.9 mmol) was added dropwise using a syringe. The slightly hazy solution was allowed to stir at room temperature under nitrogen for 17 hours. N,N-dimethyl-3-sulfo-N-(3-(trimethoxysilyl)propyl)propan-1-aminium (example 1, 3.2 g, 9.8 mmol) was dissolved in water (15 mL). This homogeneous, colorless solution was added to the tantalum containing reaction mixture dropwise but quickly under air with stirring. The flask was fitted with a condenser and then placed in an oil bath preheated to 78° C. After stirring at this temperature for 6 hours, the colorless, homogeneous reaction mixture was cooled to room temperature. Trifluoroethanol was substantially removed in a rotary evaporator after adding water (20 mL). The aqueous solution was neutralized using concentrated ammonium hydroxide and then filtered successively through 200 nm, 100 nm and then 20 nm filters. The solution was then dialyzed using 3500 MW cut-off regenerated cellulose snake skin dialysis tubing 4 times. The first dialysis was performed in 50:50 DI water to pH 7.0 phosphate buffer. Subsequent dialyses were performed in DI water. The purified nanoparticle product was not isolated from water. A percent solids test on an aliquot was used to determine that the yield of coated nanoparticles was 1.55 g. The average particle size was determined by dynamic light scattering to be 1.6 nm.

Synthesis of Tantalum Oxide-Based Nanoparticle

Step-1: Synthesis of Ethyl 2(4(3(trimethoxysilyl)propylcarbamoyl)piperazin-1-yl)acetate (3-isocyanatopropyl)trimethoxysilane (4.106 g) was added to a solution of ethylacetoxypiperazine (3.789 g) in methylene chloride (20 mL). The solution was stirred for 16 hours, and then the solvent was removed under reduced pressure, yielding 8.37 g of material that was used without further purification.

Step-2: Reaction of Ethyl 2-(4-(3-(trimethoxysilyl)propylcarbamoyl)piperazin-1-yl)acetate with Tantalum Oxide-Based Core A 500 mL round-bottom flask was charged with n-propanol (99 mL), isobutyric acid (1.4 mL), and water (1.2 mL). The solution was stirred for 5 min., then Ta(OEt)$_5$ (5.37 g) was added dropwise to the solution. The solution was stirred at room temperature under nitrogen for 18 hours. A total of 60 mL of this solution was then added to ethyl 2-(4-(3-(trimethoxysilyl)propylcarbamoyl)piperazin-1-yl)acetate (6.37 g), and the solution was stirred under nitrogen for 2 hours at 100° C. The mixture was then cooled to room temperature, water (20 mL) was added, and the mixture was stirred for 18 hours at room temperature. A total of 75 mL of 0.33 N aqueous hydrochloric acid was then added, and the solution was heated to 60° C. for 6 hours. The mixture was then cooled to room temperature, 250 mL of 28% aqueous ammonia was added, and the mixture was stirred for 5 days. The ammonia and propanol were removed under reduced pressure, then the material was poured into 3,000 MW cut-off regenerated cellulose dialysis tubing, and dialyzed against distilled water for 48 hours, changing the dialysis buffer every 12 hours. The solution was then filtered through 30,000 MW cut-off centrifuge filters, yielding particles with an average size of 4.5 nm, as measured by DLS.

Synthesis of Iron Oxide-Based Nanoparticle

Synthesis of Superparamagnetic Iron Oxide Nanoparticles

A 100 mL three-necked round bottom flask was charged with 706 mg of Fe(acac)$_3$ and 20 mL of anhydrous benzyl alcohol. The solution was sparged with nitrogen and then heated to 165° C. for 2 hours under a nitrogen atmosphere. The solution was then cooled to, and stored, at room temperature.

Reaction of Ethyl 2-(4-(3-(trimethoxysilyl)propylcarbamoyl)piperazin-1-yl)acetate with Superparamagnetic Iron Oxide A 10 mL aliquot of superparamagnetic iron oxide nanoparticles in benzyl alcohol (5.58 mg Fe/mL) was diluted with 50 mL of tetrahydrofuran. 2.00 g of ethyl 2-(4-(3-(trimethoxysilyl)propylcarbamoyl)piperazin-1-yl)acetate was added, and the mixture was heated to 60° C. with stirring for 2 hours, followed by cooling to room temperature. 50 mL of 1.0 M aqueous potassium carbonate was added after which the flask was then sealed and heated with stirring to 60° C. for 18 hours. The mixture was then cooled and centrifuged, and the aqueous layer was poured into 10,000 MW cut-off regenerated cellulose dialysis tubing and dialyzed vs 4 liters of 10 mM sodium citrate for 48 hours, changing the dialysis buffer every 12 hours. The final volume was 94 mL, with a total of 0.416 mg iron per mL of solution. The material had an average particle size of 8.4 nm in 150 mM aqueous sodium chloride as measured by dynamic light scattering.

Reaction of N,N-dimethyl-3-sulfo-N-(3-(trimethoxysilyl)propyl)propan-1-aminium with Superparamagnetic Iron Oxide A 16.75 mL aliquot of superparamagnetic iron oxide nanoparticles in benzyl alcohol (5.58 mg Fe/mL) was added to tetrahydrofuran for a total volume of 94.5 mL. This solution was then added to a pressure flask, along with 3.1 g of N,N-dimethyl-3-sulfo-N-(3-(trimethoxysilyl)propyl)propan-1-aminium, and the mixture was heated to 50° C. with stirring for 2 hours. After cooling to room temperature, a total of 31 mL of isopropanol and 76 mL of concentrated aqueous ammonium hydroxide (28% NH$_3$ in water) were added; the flask was then sealed and heated to 50° C. with stirring for 18 hours. The mixture was cooled and washed with hexanes (100 mL×3). The aqueous layer was poured into 10,000 MW cut-off regenerated cellulose dialysis tubing, and dialyzed vs 4 liters of 10 mM sodium citrate for 18 hours. The final solution had a total of 0.67 mg iron per mL of solution. The material had a particle size of 9.2 nm.

Determination of the Particle Size and Stability of the Nanoparticles in Water

Nanoparticles from method 1 (36.2 mg) were dissolved in 2 mL of DI water. The solution was filtered through a 20 nm filtration membrane. The average particle size was measured as a hydrodynamic radius by dynamic light scattering (DLS), immediately after the filtration step. The sample was stored for 15 days at 37° C., with periodic monitoring by DLS. The results are shown in Table 1.

TABLE 1

| Time (t) | Average particle size* |
|---|---|
| 0 | 10.1 nm |
| 5 days | 12.8 nm |
| 15 days | 12.2 nm |

*Average particle size was measured at 37° C., using DLS.

Nanoparticle Biodistribution Studies

In-vivo studies were carried out with male Lewis rats with a size range between 150 and 500 grams body weight. Rats were housed in standard housing with food and water ad libitum and a 12 hour day-night lighting cycle. All animals used for biodistribution were otherwise untreated, normal subjects.

Nanoparticles were administered as a filter-sterilized solution in either water or saline. Administration was performed under isoflurane anesthesia (4% induction, 2% maintenance) via a 26 G catheter inserted into the lateral tail vein. Injection volumes were determined based on the concentration of the nanoparticles in the injectate and the size of the rat, but were generally less than 10% of rodent blood volume. The target dose was 100 mg of core metal (e.g., tantalum) per kg of body weight. Once injected, animals were removed from anesthesia and, after a period of observation for adverse effects, returned to normal housing. At a later period of as short as a few minutes to as long as 6 months, the rats were euthanized, and organs of interest were harvested, weighed, and analyzed for their total metal (e.g., tantalum) content by ICP analysis. Along with the organs, a sample of the injected material was submitted to determine the exact concentration of injectate. These combined data determined the percentage of the injected dose ("% ID") remained in a tissue of interest. These data were reported either as % ID/organ, or % ID/gram of tissue. Experiments were generally performed with four duplicate rats at each time-point, allowing for the determination of experimental error (±standard deviation).

TABLE 2

| Coating | Kidney (% ID/organ) | Liver (% ID/organ) | Spleen (% ID/organ) |
|---|---|---|---|
| Diethylphosphatoethyl-triethoxysilane (PHS) | 4.2 ± 0.43 | 2.57 ± 0.64 | 0.16 ± 0.05 |
| N,N-dimethyl-3-sulfo-N-(3-(trimethoxy-silyl)propyl)propan-1-aminium (SZWIS) | 0.29 ± 0.05 | 0.24 ± 0.02 | ND |
| N-(2-carboxyethyl)-N,N-dimethyl-3-(trimethoxysilyl)propan-1-aminium (CZWIS) | 0.70 ± 0.47 | 0.33 ± 0.03 | 0.04 ± 0.01 |

Table-2 describes the biodistribution of fractionated nanoparticles with non-zwitterionic (PHS) and zwitterionic coatings (SZWIS and CZWIS) in major clearing organs at 1 week following IV injection. "ND" stands for "not detected".

The amount of tantalum retained per organ is represented in the Table-2 as the fraction of the injected dose. Comparably sized non-zwitterionic coated nanoparticles are retained at much higher levels (almost one order of magnitude) than either of the zwitterionic coatings tested.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for making a plurality of nanoparticles having a core-shell structure, the method comprising:
   a) providing a core precursor material comprising a transition metal alkoxide for generating a core having a core surface essentially free of silica;
   b) providing a shell precursor material comprising a tri-alkoxy silane-functionalized zwitterionic compound; and
   c) reacting the core precursor material with the shell precursor material in presence of an acid to generate the plurality of nanoparticles having a core-shell structure, wherein the tri-alkoxy silane-functionalized zwitterionic compound binds to the core of the nanoparticle at the core surface without any intervening silica layer.

2. The method of claim 1, further comprising providing a zwitterionic compound and a silane compound, and reacting the zwitterionic compound with the silane compound to produce the tri-alkoxy silane-functionalized zwitterionic compound used in part (b) of claim 1.

3. The method of claim 2, further comprising hydrolysing the zwitterionic compound before reacting it with the silane compound to form the tri-alkoxy silane functionalized zwitterionic moiety used in part (b) of claim 1.

4. The method of claim 1, wherein the tri-alkoxy silane-functionalized zwitterionic compound comprises a positively charged moiety, a negatively charged moiety and a first spacer group in between the positively charged moiety and the negatively charged moiety.

5. The method of claim 4, wherein the positively charged moiety comprises protonated primary amines, protonated secondary amines, protonated tertiary alkyl amines, protonated amidines, protonated guanidines, protonated pyridines, protonated pyrimidines, protonated pyrazines, protonated purines, protonated imidazoles, protonated pyrroles, quaternary alkyl amines, or combinations thereof.

6. The method of claim 4, wherein the negatively charged moiety comprises deprotonated carboxylic acids, deprotonated sulfonic acids, deprotonated sulfinic acids, deprotonated phosphonic acids, deprotonated phosphoric acids, deprotonated phosphinic acids, or combinations thereof.

7. The method of claim 4, wherein the first spacer group comprises alkyl groups, aryl groups, substituted alkyl and aryl groups, heteroalkyl groups, heteroaryl groups, carboxy groups, ethers, amides, esters, carbamates, ureas, straight chain alkyl groups of 1 to 10 carbon atoms in length, or combinations thereof.

8. The method of claim 4, wherein a silicon atom of the tri-alkoxy silane-functionalized zwitterionic compound is connected to the positively or negatively charged moiety via a second spacer group.

9. The method of claim 8, wherein the second spacer group comprises alkyl groups, aryl groups, substituted alkyl and aryl groups, heteroalkyl groups, heteroaryl groups, carboxy groups, ethers, amides, esters, carbamates, ureas, straight chain alkyl groups of 1 to 10 carbon atoms in length, or combinations thereof.

10. The method of claim 1, wherein the tri-alkoxy silane-functionalized zwitterionic compound comprises N,N-dimethyl-3-sulfo-N-(3-(trimethoxysilyl)propyl)propan-1-aminium, 3-(methyl(3-(trimethoxysilyl)propyl)amino)propane-1-sulfonic acid, 3-(3-(trimethoxysilyl)propylamino)propane-1-sulfonic acid, 2-(2-(trimethylsilyl)ethoxy(hydroxy) phosphoryloxy)-N,N,N-trimethylethanaminium, 2-(2-(trimethoxysilyl)ethyl(hydroxy) phosphoryloxy)-N,N,N-trimethylethanaminium, N,N,N-trimethyl-3-(N-3-(trimethoxysilyl)propionylsulfamoyl)propan-1-aminium, N-((2H-tetrazol-5-yl)methyl)-N,N-dimethyl-3-(trimethoxysilyl)propan-1-aminium, N-(2-carboxyethyl)-N,N-dimethyl-3-(trimethoxysilyl)propan-1-aminium, 3-(methyl(3-(trimethoxysilyl)propyl)amino)propanoic acid, 3-(3-(trimethoxysilyl)propylamino)propanoic acid, N-(carboxymethyl)-N,N-dimethyl-3-(trimethoxysilyl)propan-1-aminium, 2-(methyl(3-(trimethoxysilyl)propyl)amino)acetic acid, 2-(3-(trimethoxysilyl)propylamino)acetic acid, 2-(4-(3-(trimethoxysilyl)propylcarbamoyl)piperazin-1-yl)acetic acid, 3-(4-(3-(trimethoxysilyl)propylcarbamoyl)piperazin-1-yl)propanoic acid, 2-(methyl(2-(3-(trimethoxysilyl)propylureido)ethyl)amino) acetic acid, 2-(2-(3-(trimethoxysilyl)propylureido)ethyl)aminoacetic acid, or combinations thereof.

11. The method of claim 1, wherein the core comprises tungsten, tantalum, hafnium, zirconium, molybdenum, silver, zinc, or combinations thereof.

12. The method of claim 1, wherein the core comprises tantalum oxide.

13. The method of claim 1, wherein the core comprises a superparamagnetic material.

14. The method of claim 13, wherein the superparamagnetic material comprises iron, manganese, copper, cobalt, nickel, or combinations thereof.

15. The method of claim 1, wherein the core comprises a superparamagnetic iron oxide.

16. The method of claim 1, wherein the plurality of nanoparticles has a median particle size up to about 50 nm.

17. The method of claim 1, wherein the plurality of nanoparticles has a median particle size up to about 10 nm.

18. The method of claim 1, wherein the plurality of nanoparticles has a median particle size up to about 6 nm.

19. The method of claim 1, further comprising fractionating the plurality of nanoparticles, wherein the fractionating comprises filtering the plurality of nanoparticles.

20. The method of claim 1, further comprising purifying the plurality of nanoparticles to form a plurality of purified nanoparticles.

21. The method of claim 20, wherein the purifying comprises use of dialysis, tangential flow, filtration, or diafiltration.

22. The method of claim 20, further comprising isolating the purified nanoparticles.

* * * * *